US008846405B2

(12) United States Patent
Martinez, II et al.

(10) Patent No.: US 8,846,405 B2
(45) Date of Patent: Sep. 30, 2014

(54) METHOD AND APPARATUS FOR THE IDENTIFICATION OF ALDEHYDES

(75) Inventors: Enrique Martinez, II, Clinton Township, MI (US); Denis Callewaert, Metamora, MI (US); Donald J. VerLee, Libertyville, IL (US)

(73) Assignee: Oxford Biomedical Research, Inc., Rochester Hills, MI (US)

( * ) Notice: Subject to any disclaimer, the term of this patent is extended or adjusted under 35 U.S.C. 154(b) by 23 days.

(21) Appl. No.: 13/550,342

(22) Filed: Jul. 16, 2012

(65) Prior Publication Data
US 2014/0017800 A1 Jan. 16, 2014

(51) Int. Cl.
*G01N 21/75* (2006.01)
*G01N 21/00* (2006.01)

(52) U.S. Cl.
USPC .......................................... 436/128; 436/127

(58) Field of Classification Search
CPC .......... G01N 2333/00; G01N 2333/90; G01N 2333/9104; G01N 2001/00; G01N 2001/28; G01N 2021/00
USPC ................................................ 436/128, 127
See application file for complete search history.

(56) References Cited

U.S. PATENT DOCUMENTS 4,471,055 A * 9/1984 Opp .............................. 436/128
4,753,891 A * 6/1988 Thompson et al. ........... 436/130
5,726,063 A * 3/1998 Gerard-Monnier et al. .. 436/128

OTHER PUBLICATIONS

Enrique Martinez, II et al., "A Highly-Sensitive and Specific Colorimetric Assay for Malonaldehyde. Society for Free Radical Biology and Medicine", Orlando FL. Nov. 2010.
Enrique Martinez, II et al., "Improved Methods for Performing the 2-Thiobarbituric Acid Reactive Substances (TBARS) Assay". Orlando, FL. Nov. 2010.
Enrique Martinez, II et al., "A Highly-Sensitive and Specific Colorimetric Assay for Malonaldehyde", Oxford Biomedical Research. Orlando, FL. Nov. 2010.
Enrique Martinez, II et al., "Improved Methods for Performing the 2-Thiobarbituric Acid Reactive Substances (TBARS) Assay", Oxford Biomedical Research. Orlando, FL. Nov. 2010.

* cited by examiner

*Primary Examiner* — Christine T Mui
(74) *Attorney, Agent, or Firm* — Greer, Burns & Crain, Ltd.

(57) ABSTRACT

A method for detecting the presence of an aldehyde in a sample comprises steps of exposing the sample at room temperature to a test medium to catalyze the formation of optically detectable quantities of a product within a time period of no more than 60 minutes and without applying any external heat to the sample or test medium, the test medium comprising a indicator that is a nucleophilic compound having acidic protons at the nucleophilic center and at least one acid, and measuring the optical changes that occur as a result of the catalysis.

23 Claims, 15 Drawing Sheets

METHOD AND APPARATUS FOR THE IDENTIFICATION OF ALDEHYDES

FIELD

A field of the invention is the identification of aldehydes. An additional field is the estimation of the concentration of an aldehyde in a sample. Further fields include apparatuses for identifying or quantifying aldehydes.

BACKGROUND

Aldehydes are present in a wide range of substances, including body fluids (e.g. blood, urine, tears), breath, agricultural materials, meat, fish, poultry, and other commercial and natural goods. The production of aldehydes is a natural process in many materials that is related to various biologic, biochemical, and related conditions. The presence and/or concentration of an aldehyde in a material can therefore be useful to determine a biologic, biochemical, medical, or other status of the material (or material generating entity). As an example, the concentration of one or a group of these substances has a range of applications ranging from the assessment of oxidative stress in a living being to monitoring the relative freshness or potential adulteration of agricultural products (e.g., meat, fish, poultry, crops).

By way of a particular example application, oxidative stress (OS) is a term used to describe the level of damage in living organisms caused by reactive oxygen species at molecular and cellular levels. The level of OS can be determined by measuring certain biomarkers including, but not limited to, malondialdehyde (MDA) a dialdehyde with a three-carbon backbone. Oxidative stress biomarkers including MDA are present in many biological fluids, such as urine, blood, breath and tears.

While a variety of methods and apparatuses have been developed to determine the presence and/or concentration of aldehydes in these and similar applications, the known art suffers from various problems and undesirable characteristics. These include, but are not limited to one or more of: (a) lack of specificity, (b) the need for significantly elevated temperatures, (c) the use of strong acids, (d) complexity of testing/handling/storage requirements, (e) interference with the test results by unrelated compounds and background conditions, (f) unwanted (and sometimes interfering) byproduct(s) from test reagent(s), and (g) the time required for testing.

SUMMARY

Embodiments of the present invention include methods and apparatuses that address many unresolved problems in the art. Embodiments include methods and apparatuses that achieve (a) greater specificity in the identification and/or quantification of aldehyde or group of aldehydes measured—including a significant reduction in the generation of a signal due to the interaction of acids with unrelated substances in the test sample as well as improved selectivity for certain aldehydes or classes of aldehydes and a significant increase in the sensitivity for specific aldehydes to enable measurement of their presence at levels that are relevant for assessment of OS and for other applications, (b) a significant reduction in the hazards associated with such determinations, (c) faster determinations, and (d) determination of specific aldehydes or classes of aldehydes quickly and conveniently, including in test devices that do not require a highly skilled operator and complex laboratory operations.

One embodiment of a method of the invention is a method for detecting the presence of an aldehyde in a sample comprising the steps of exposing the sample at room temperature to a test medium to catalyze the formation of optically detectable quantities of a product within a time period of no more than 60 minutes and without applying any external heat to the sample or test medium, the test medium comprising an indicator that is a nucleophilic compound having acidic protons at the nucleophilic center and at least one acid; and measuring the optical changes that occur as a result of the catalysis.

Another example embodiment of the invention is a method for determining the presence of an aldehyde comprising the steps of reacting a nucleophilic compound having acidic protons at the nucleophilic center and a sulfonic acid with an aldehyde to cause changes in optical properties; and measuring the optical property changes. Still another example embodiment of the invention is an apparatus for estimating the concentration of an aldehyde comprising a solid medium; a nucleophilic aromatic compound held on the medium; and an acid held on the medium.

BRIEF DESCRIPTION OF THE DRAWINGS

FIG. 1a depicts the reaction mechanism for the formation of a 1:2 complex between MDA and the indicator 2-thiobarbituric acid, while FIG. 1b depicts the reaction between MDA and the indicator 1-methyl-2-phenylindole;

FIG. 5 illustrates the use of specific optical properties to selectively detect or quantify malonaldehyde-indicator products vs. a non-aldehyde compound containing a carbonyl group (acetone in this example).

FIG. 6 is a chart illustrating the utility of invention embodiments employing an aromatic amine indicator for the analysis of a group of carbonyl-containing compounds based on the absorbance of light at a specific wavelength for the selective detection or quantification of malonaldehyde.

DETAILED DESCRIPTION

Before discussing example embodiments of the invention in detail, it will be appreciated that invention embodiments may take the form of methods and of apparatuses. Some methods of the invention include carrying out steps of a chemical reaction, while some related apparatuses of the invention include chemical reagents held on a solid media useful to carry out such reactions. There may be overlap between such embodiments, with an example being that a method of the invention may include steps of using an apparatus of the invention, and vice-versa. It will therefore be understood that when describing a method of the invention, description of a related apparatus of the invention may also be had, and vice-versa.

Turning now to example invention embodiments, one is a method of identifying an aldehyde and comprises steps of reacting a nucleophilic indicator compound and an acid with an aldehyde to produce a change in optical properties that can be measured. In some embodiments, an additional catalyst, initiator and/or signal-enhancing component is further provided. Reagents may be provided either in solution or held on (with an example including, but not limited to, within interstitial spaces of) a solid support. Other embodiments of the invention are directed to apparatuses for identifying a specific aldehyde or groups of aldehydes.

Figure 1A:
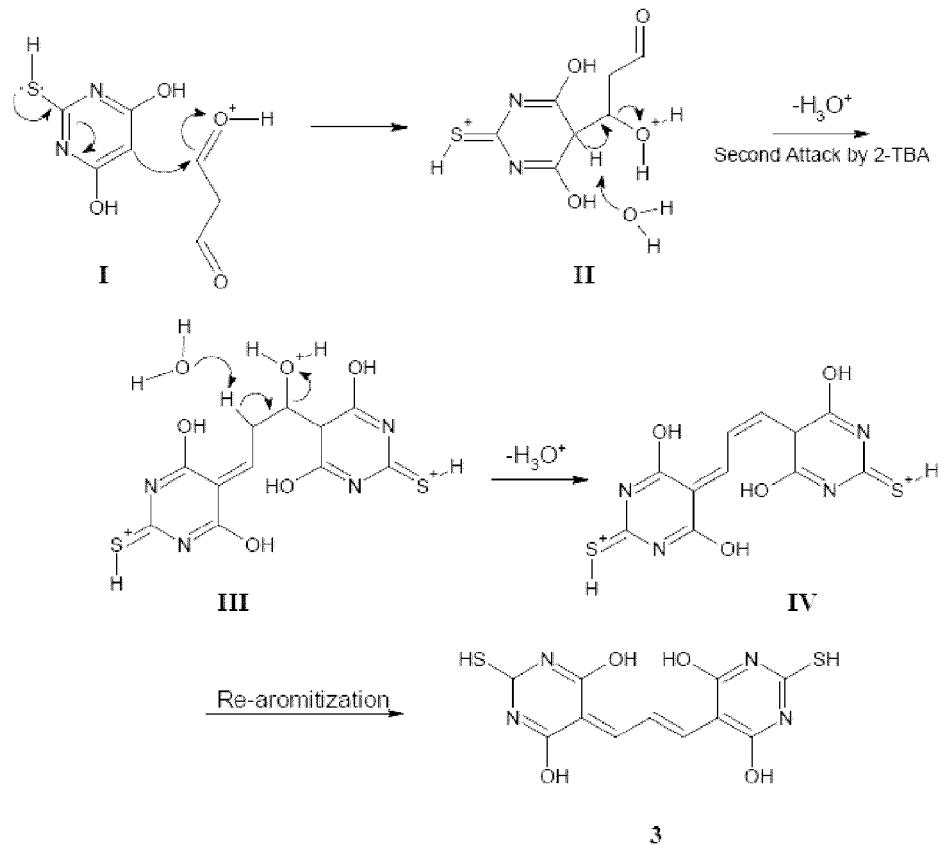
FIGS. 1a and 1b depict chemical reactions for an invention embodiment involving active methylene compounds forming specific products with the aldehyde malonaldehyde (MDA).
Figure 1B:
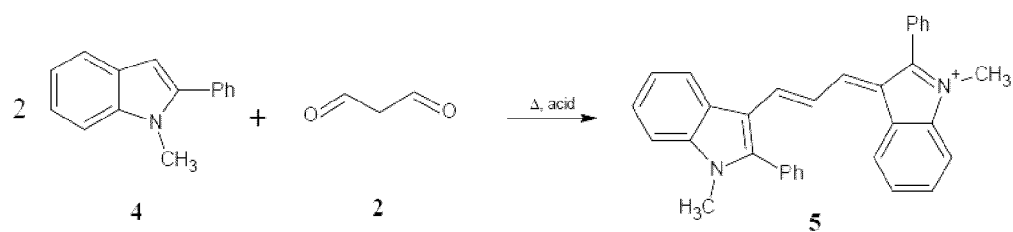
Figure 2:
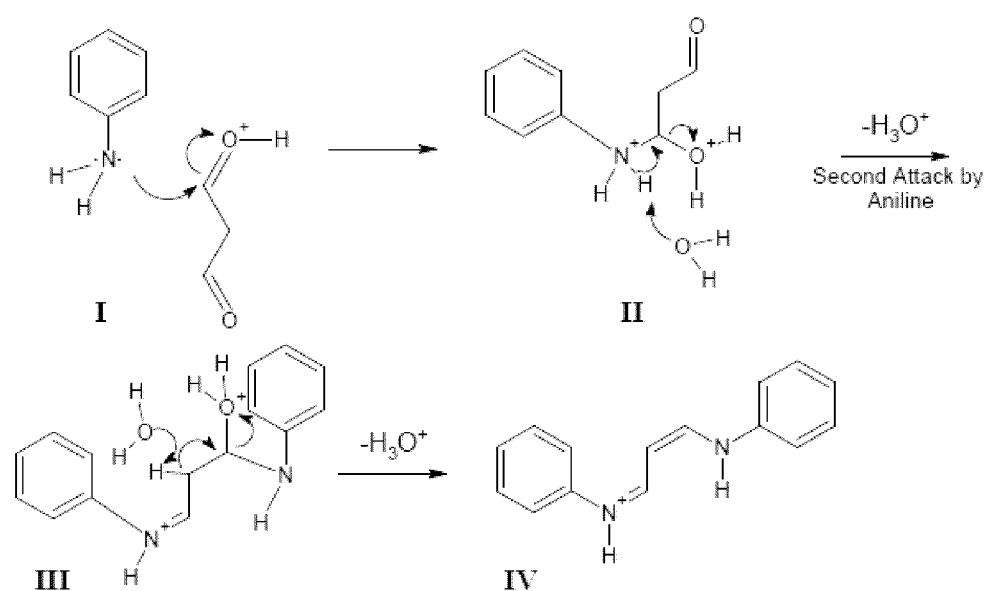
FIG. 2 depicts the reaction mechanism for an invention embodiment involving two molecules of an aromatic amine compound indicator and the aldehyde MDA.

For purposes of initial illustration, one particular example embodiment of the invention is illustrated in FIG. 1 as a chemical reaction schematic. With this embodiment in mind, further details of various individual elements can be presented. Referring now to the reaction schematic of FIG. 1a, two molecules of 2-thiobarbituric acid (2-TBA) (or other active methylene compound, as illustrated in FIG. 2), combine with one molecule of malondialdehyde under acidic conditions. A reaction between the indicator molecule (the 2-TBA or other activated methylene compound) and the aldehyde cause a product to form that has different optical properties, as compared to reactants, that can be measured.

One method embodiment illustrated in FIG. 1 is performed as follows: A solution is prepared by dissolving 100 mg of stannous chloride (or other reducing agent, although stannous chloride is believed to assist stability of liquid or solid formulations), 3.0 g of the aryl sulfonic acid (or other suitable acid) and 150 mg of the active methylene compound in a suitable solvent. An example solvent is water, another is a 50%/50% mix of water and dimethylsulfoxide, and many other solvents are possible.

As shown in Scheme I, FIG. 1a, the active methylene group of the indicator molecule attacks a protonated malonaldehyde at the carbonyl forming a carbon-carbon bond. Further protonation of the newly formed hydroxyl group converts the single carbon-carbon bond to a double bond (Scheme II, FIG. 1a). A second indicator molecule then attacks the other carbonyl group on the malonaldehyde molecule, and the process is repeated, with subsequent loss of water (Scheme III, FIG. 1a). The final chromophore (3, FIG. 1a) is then formed by re-aromitization of the carbon backbone.

The example embodiment of FIG. 1a can be carried out in liquid phase, or can be carried out using a solid medium holding reactants (either in solid or liquid phase, with an example being within interstitial spaces). In either case, it can occur at room temperature in a period of no more than 5 mins, no more than 10 mins, no more than 15 mins, no more than 20 mins, no more than 30 minutes, no more than 40 minutes, no more than 60 minutes, or other periods depending on various conditions including temperature, reagent concentrations and others. As used herein, the term "room temperature" is intended to have its ordinary meaning. Room temperature may be, for example, approximate indoor environmental temperature without applying any excessive heat or cooling.

In a liquid phase embodiment, one volume of the prepared solution (the stannous chloride/aryl sulfonic and active methylene compound in a suitable solvent solution) is added to the same volume of the sample or standard to be analyzed. After mixing, the sample may become turbid, depending on the nature of the sample. For samples that may become turbid, after 20 minutes at room temperature, the samples are centrifuged to remove any suspended solids. The quantity of the product formed (IV in FIG. 1 for TBA as indicator, or 5 in FIG. 1b) for an indole-containing indicator is determined by measuring the optical changes (e.g. the change in absorbance at ~532 nm, or the fluorescence at ~585 nm produced by excitation at ~532 nm when using 2-thiobarbituric acid). The specific absorbance maximum for the chromogenic product (depends on the solvent and acid used (i.e. is dependent on a solvochromatic shift).

When testing in the solid phase, a solution of 400 mg of 2-TBA and 400 mg of para-toluenesulfonic acid are dissolved in 10 ml of methanol. This solution is impregnated into a suitable solid support and the solvent is evaporated. Impregnation may include, for example, placement into interstitial spaces of a solid matrix support. The sample is then applied to the solid matrix (e.g. by dipping, spraying or other application step) and the reaction is allowed to react for a fixed time interval (e.g. five minutes), and the reflectance or fluorescence is measured at the appropriate wavelength for that particular indicator agent. Alternatively, the reflectance or fluorescence is monitored as a function of time, and the rate of change of the reflectance or fluorescence during an interval in which the rate of generation of the final product is proportional to the concentration of the aldehyde.

The assay using 2-thiobarbituric acid, as an example, will produce a stable chromophore within less than 60 minutes at room temperature and give acceptable measurements for several hours after mixing. Notably, in some embodiments, the temperature of the solution may rise due to heat of dissolution and/or reaction, but no external heat is required or is applied. In some embodiments, the temperature does not exceed 50° C. during the reaction period. In other embodiments, the temperature does not exceed 30° C., in others 40° C., and other temperatures in others. Depending on the nucleophilic indicator used and the aldehyde(s) to be analyzed, the time for completion of the reaction as well as the wavelength of the maximum absorbance will vary.

Having now presented specific example embodiments for frame of reference, further details of these and various other embodiments can be discussed and illustrated.

Sample Containing Aldehyde:

Invention embodiments are believed to have a wide range of utility in a variety of applications in which indication of the presence and/or estimation of concentration of an aldehyde is useful. As used herein, the term "an aldehyde" is intended to refer to any compound that may be chemically characterized as containing one or more aldehyde functional groups. In some embodiments, a pass/fail type indication will be made indicating that some minimum concentration of a specific aldehyde or group of aldehydes is present. In others, an estimation of the concentration is made. Different embodiments are designed to be specific for specific aldehyde(s), for groups of aldehyes of interest, or for all aldehydes in a sample.

As an example, many invention embodiments are designed to specifically measure the presence and/or concentration of malonaldehyde, an unsaturated molecule with two aldehyde functional groups, from biologic samples (urine, blood, saliva, others). This is useful for indicating oxidative stress in living beings. Other invention embodiments are designed to measure other various compounds containing one or more aldehyde groups, including saturated and/or unsaturated molecules, as biomarkers for various diseases and conditions. The aldehyde concentration in human breath, for example, may serve as a biomarker useful to screen for the presence of lung cancer. Other applications include food and agricultural related products. The oxidation of oils has important effects on the quality of oily foods. Such oxidation generates aldehydes, including the unsaturated aldehydes 2-heptenal, 2-octenal, 2-decenal, 2-undecenal and 2,4-decadienal, and/or trans molecules of these compounds. Similarly, levels of formaldehyde and acetaldehyde in fish and seafood can indicate quality. Lipids present in foods react with oxygen and other substances to produce aldehydes, and the level of lipid oxidation (and hence the concentration of aldehydes) can be indicative of food quality. Other applications include environmental and others in which aldehyde presence in gasses or liquids can be indicative of gas or liquid quality or pollution thereof.

Nucleophilic Compound:

Certain types of nucleophilic compounds have been discovered to have utility as indicators in invention embodiments in that they react with aldehyde(s) to give a product that has specific optical properties, undergoing a change through reaction to yield an indicator-aldehyde product with optical properties (color, reflectance/absorbance, fluorescence, other) that are distinct from the unreacted indicator and that change in intensity in proportion to the quantity of the indicator-aldehyde product formed. An example nucleophilic compound has acidic protons at the nucleophilic center, the nucleophilic being one of C or N. Many suitable nucleophilic compounds are organic compounds with unsaturated bonds.

Some example nucleophilic compounds suitable for use in invention embodiments include (but are not limited to):
  active methylene compound,
  barbituric acid and its derivatives
  1-methyl-2-phenylindole
  an aromatic amine
  a Shiff reagent
  fuchsin
  aniline
  4'-aminoacetophenone
  ethyl p-aminobenzoate
  4,4'-sulfonyldianiline
  p-nitroaniline
  azulene
  4-hexlylresourcinol
  N-methylpyrrole
  indole Some Particular examples include aromatic amines and active methylene compounds. Suitable aromatic amines include an aniline backbone, with other ring substituents selected to not interfere with nucleophilicity of the nucleophilic center (at the nitrogen center). Also, it has been discovered that it is useful if the product formed upon reaction of the aromatic amine with aldehyde(s) does not absorb light or fluoresce in the same region as the aldehyde or the unreacted indicator. Some particular nucleophilic compounds that are believed to offer good utility in some invention embodiments include the N-methyl-2-phenylindole family of heterocyclic compounds, 4-aminophenylsulfone and 2-thiobarbituric acid.

Aryl amines are believed to offer particular utility in many applications. FIG. 2 illustrates a sample method of the invention that is largely identical in sequence to that of FIG. 1, but with an aromatic amine as the nucleophilic indicator compound (instead of an active methylene containing compound such as 2-thiobarbituric acid of FIG. 1). The reaction sequence that gives rise to C—N bonds between the indicator and the aldehyde of FIG. 2 has a lower activation energy and is thus faster than the formation of C—C bonds between the indicator and the aldehyde for active methylene compounds as depicted in FIG. 1 when run using the same conditions, going to completion in less than 5 minutes in most embodiments. Referring to FIG. 2, one molecule of the aromatic amine attacks a molecule of malonaldehyde, followed by loss of water to form an imine bond. This attack is repeated by a second equivalent of the aromatic amine, to form structure IV. This structure shows optical property changes as compared to the initial aromatic amine structure which can be measured. As with the reaction scheme of FIG. 1, the reaction scheme of FIG. 2 may be carried out in a solid phase invention embodiment with reactants (either solid or liquid phase) held on a solid medium.

Acid:

The unexpected benefits and advantages of particular acids used in various invention embodiments represent a significant and important discovery. A variety of different acids will prove useful in different invention embodiments, but sulfonic acids are believed to offer significant utility in many embodiments, particularly when used with an active methylene nucleophilic compound and particularly when solid phase invention embodiments are practiced. Aryl sulfonic acids and substituted aryl sulfonic acids including para-toluene sulfonic acid ("tosic" or "tosylic" acid), and benzene sulfonic acid are particular examples. The advantages of aryl sulfonic acids, with tosic being one example, are significant and unexpected. Many disadvantages of the prior art, including the need for strong acids, significantly elevated temperatures, and long reaction times are addressed at least in part by the surprising discovery of the utility of aryl sulfonic acids and others in invention embodiments.

It is reasonable to expect that reaction rate would be shortened with increasing acid strength, as a greater concentration of $H^+$ is available for reaction. Through the present invention, however, it has surprisingly been discovered that this is not always the case in various invention embodiments. Aryl sulfonic acids (including tosic acid) have been discovered to surprisingly achieve reaction rates that can be orders of magnitude better than stronger acids, which allows for very fast reaction times at much lower temperatures (which in some cases can be room temperature) than was possible in the prior art, as well as other advantages.

Experiments performed using several different acids having various strengths (expressed as pKa) illustrate this. The acids were prepared as 1.0 normal solutions in water. Then 1.0 ml of each of the acids in aqueous dimethylsulfoxide solutions was combined with 100 microliters of an 80 mg/ml solution of 2-thiobartburic acid in a cuvette and the absorbance reading set to zero at 532 nm. To this solution 100 microliters of a 1.28 micromolar solution of malondialdehyde in water was added. Eight cycles of pipette mixing were performed, and measurement of the absorbance values at 532 nm started. The time to reach an absorbance of 0.8 at 532 nanometers was recorded. Results are plotted against acid according to pKa in FIG. 3.

Figure 3:
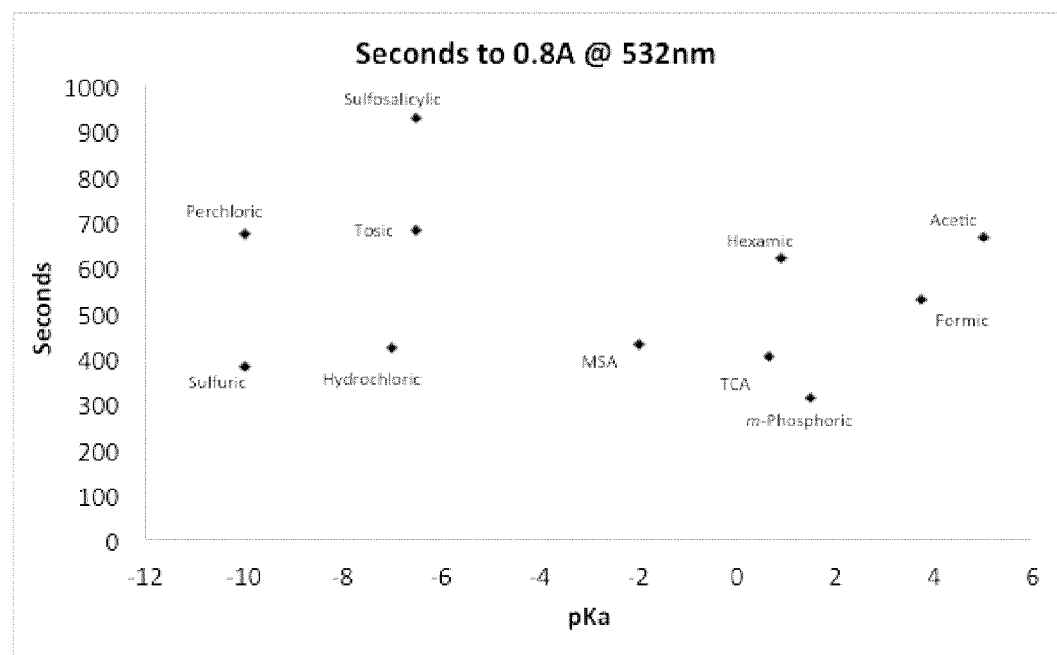
FIG. 3 is a chart illustrating the unexpected discovery of a lack of correlation between the pKa of acids with the rate of product formation for liquid phase embodiments of the invention involving a 2-thiobarbituric acid indicator to measure MDA.

As indicated by FIG. 3, it has surprisingly been discovered that strength of acid does not linearly correlate with reaction rate. The fastest reaction rate was surprisingly discovered to correspond to the third weakest acid tested, m-phosphoric.

Although tosic acid fell somewhere near the middle of reaction rates of those tested and summarized on the graph of FIG. 3, it has been discovered to be advantageous to the other acids in many other ways for many invention applications. For example, it is generally less hazardous, less corrosive, and much easier to handle than several of the others. Also, with regard to urine sample testing, its reaction color distinction from urine is excellent—the background urine coloring can be readily distinguished for measurement purposes. An additional important advantage of tosic acid relates to use in invention embodiments that utilize solid phase testing. Tosic acid offers advantages including:

solid phase at room temperature and pressure
relatively easy to apply to a solid matrix and to evaporate the solvent
provides good stability, including the absence of acid-catalyzed degradation of useful solid matrices at ambient temperatures
easy to handle in solid form Although tosic acid has proven to have particularly favorable performance in invention embodiments, the precise mechanistic reasons for this are presently not known with certainty. A number of the acids shown to be effective contain a sulfonic acid functional group, which may provide an advantage, especially when 2-TBA is employed as the indicator, that independent of the strength of the acid. However, comparison of the rates obtained for equinormal concentrations of the sulfur containing acids tosic acid and hexamic acid, for example, indicates that this is not simply due to the presence of a sulfonic acid group. Again, for tosic acid, it represents a surprising result in that it has proven more effective than stronger acids. It is believed that at least part of the reason relates to the chemical structure of tosic acid including an aromatic, generally flat, conjugated configuration. It features a relatively flat plane with electrons oriented on top and bottom of the plane, which leads to a transition state that is very accessible for some of the example nucleophilic compounds used in invention embodiments, including aromatic amines such as 2-thiobarbaturic acid. It is postulated that the tosic acid and nucleophilic compound (particularly an aromatic amine or 2-thiobarbituric acid) may form a complex through pi-pi electron cloud stacking that aids reaction by lowering the transition state energy. It is believed many other similar aryl sulfonic acids will have similar utility, with perhaps hundreds of particular species able to be synthesized and suitable for use.

Figure 4:
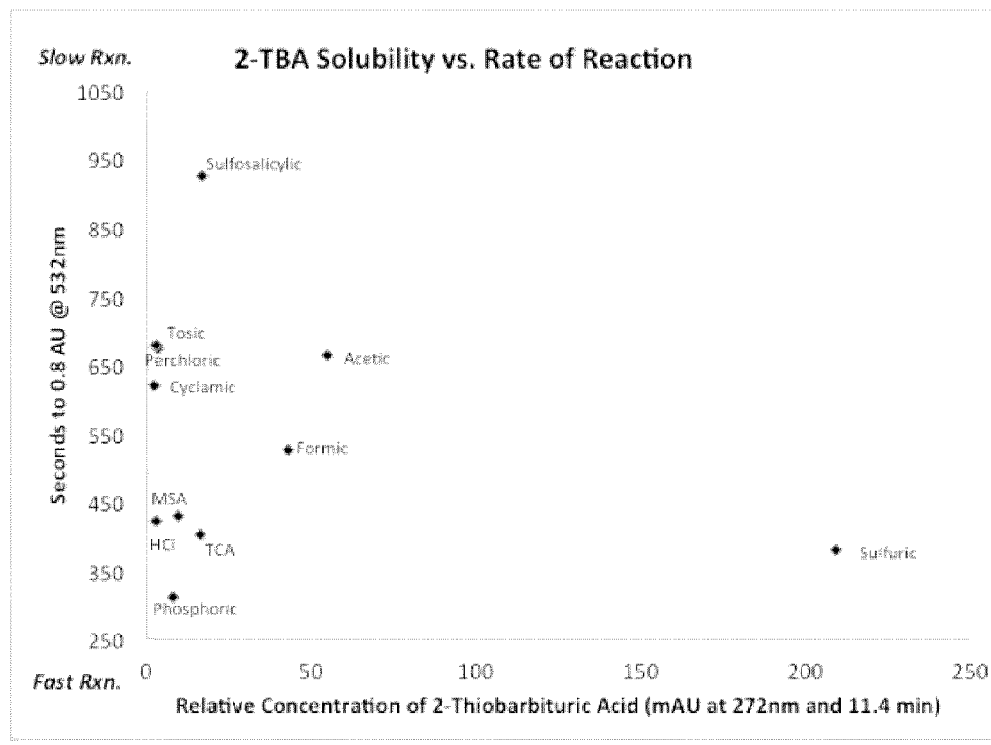
FIG. 4 is a chart illustrating the solubility of 2-thiobarbituric acid indicator used in one embodiment of the invention in 1.0 normal solutions of various acids that can promote catalysis of the formation of 2-thiobarbituric acid—aldehyde products and the lack of a correlation between the solubility of 2-TBA in a given acid and the catalytic rate of formation of a chromogenic with MDA.

The relative rate of the reaction of the indicator 2-TBA with malonaldehyde is plotted as a function of the solubility of 2-TBA in 1 N solutions of various acids FIG. 4.

Given that 2-TBA has limited solubility in aqueous solutions, one might expect that acids in which 2-TBA is more soluble would permit the use of greater concentrations of this reactant, thereby increasing the rate of its reaction with MDA. Surprisingly, no such correlation was observed. Indeed, some acids in which 2-TBA is least soluble, including tosic acid, prove to be useful for the present invention.

Further, other acids including those described on the chart of FIG. 3 will prove useful in some invention embodiments. The use of m-Phosphoric acid, as an example, provides to a very fast reaction. Although this acid may be difficult to use in solid form, at times it may have utility in some liquid phase invention embodiments and even some solid phase embodiments.

In certain embodiments that employ an aromatic amine indicator, acids that have a pKa that is greater (weaker acids) than tosic acid, may be desirable. For example, in an embodiment that involves the acid and the indicator immobilized in a solid matrix, and in which the indicator is an aromatic amine, a small concentration of a weak acid, such as hexamic acid, that can be applied to a dry matrix has certain advantages. Since the products produced by the reaction of many aromatic amines with aldehydes absorb light in the yellow region of the spectrum and samples of interest (e.g., urine or cooking oils) have varying amounts of natural yellow color, it is desirable to either measure the amount of endogenous yellow color in the sample and subtract it from the result after and end-point reaction with an aromatic amine indicator, or to perform the reaction under very weakly acidic conditions and measure the rate of color development thereby eliminating the baseline color inherent in the sample.

Catalyst/Initiator/Solvent/Stabilizer:

Some invention embodiments further benefit from the presence of a catalyst and/or initiator and/or solvent. As an example, dimethylsulfoxide (DMSO) has been discovered to offer particular utility and unexpected benefits in some invention embodiments. DMSO may be present in solid or liquid form in different embodiments. In some embodiments, the DMSO is present as a solid or an encapsulated liquid), and dissolves in an aqueous or other sample at room temperature. The dissolution creates heat energy through solvation, which heat speeds the reaction rate. In some invention embodiments the DMSO is present in an approximate 50/50 molar ratio with water solvent.

The highly polar nature of DMSO allows for it to dissolve much more (perhaps an order of magnitude more) of nucleophilic compounds such as 2-thiobarbituric acid. Additionally, in applications for aldehyde detection in protein containing samples, use of dimethylsulfoxide as a solvent/initiator/catalyst eliminates the need to deproteinate the sample before the reaction.

The effects of DMSO are not believed to be limited to contributing heat energy and aiding in dissolving of the nucleophilic compound to speed reaction rate. Experimentation has confirmed that the presence of DMSO further speeds the reaction. This is a surprising result since some solvents that are similar in polarity to DMSO do not work nearly as well, with an example being acetonitrile. The precise reason for and chemical mechanism in which DMSO functions is not clear, although it is suspected to relate at least partially to either through transition state energy lowering or some other complexation effect. It is believed, therefore, that DMSO may function as one or both of an initiator and a catalyst in addition to functioning as a solvent. The presence of a sulfur containing functional group in DMSO should also be noted and, as with tosic and hexamic acids, may play a role in the mechanism of its action in this embodiment.

Other catalysts, initiators and solvents are also believed to be useful in other invention embodiments.

In embodiments of the present invention that involve immobilizing the reactants on a solid support, it has been discovered that the indicator and aid composition is improved by the inclusion of a mild reducing agent, which prolongs the shelf life of the apparatus. One example reducing agent is stannous chloride, which is further advantageous in that it enhances the acidic environment upon addition of a liquid sample to the apparatus.

Optical Measurement/Specificity/Reduction of Interference:

The present invention significantly reduces interference, compared to prior art, in the detection and measurement of aldehydes. Prior methods that employed the application of high external heat sources (typically 60° to 100° C.) for prolonged periods to complex samples (such as biofluids or food and agricultural samples) suffer from multiple sources of interference. Interference may involve colored molecules present in the sample that absorb, reflect or fluoresce at wavelengths employed for the analysis of one or multiple aldehydes, resulting in an uncorrectable measurement result. Additional uncorrectable measurement values may result from the reaction or decomposition of non-aldehyde compounds in the sample due to the heat and acid employed, thereby producing a color change similar to that obtained from the specific reaction of indicators shown in FIGS. 1 and 2, but that are independent of the indicator for aldehyde(s).

Negative interference in the analysis of a specific aldehyde, such as malonaldehyde, can also occur. For example, prior art assays that employ heating of the sample in a strong acid, can create high concentrations of other aldehydes, or substances that may yield aldehyde(s) (e.g the accelerated conversion of glucose from the predominant acetal form to the free aldehyde form). Such substances, especially if present at high concentrations relative to the aldehyde whose specific measurement is desired, dominate the signal in the measured result to the point where correction to measure the desired aldehyde can be nearly impossible. (e.g. glucose is present in blood at concentration typically ~100 mg/dL, and may be much higher in blood and in urine samples for diabetic individuals; in contrast, levels of malonaldehyde in health and unhealthy individuals are typically less than 100 µg/dL, which is three orders of magnitude lower than glucose). Even if restricted wavelengths are employed to measure only products derived from the reaction of one malonaldehyde molecule and two indicator molecules, the presence in the sample of relatively very high amounts of other compounds that may react with an indicator using methods described in the prior art can compete with MDA for the indicator molecule. This can result in an artificially high value if the optical measurement is not restricted based on the properties of the indicator-malonaldehyde product, or in an artificially low value if only the malonaldehyde-indicator is measured (due to competition for the indicator by other substances such as glucose).

Some invention embodiments address these major defects in prior methods by the use of lower temperature and the selection of acid. They also further enhance the specificity by employing optical measurement to restrict the analysis to only malonaldehyde-indicator product or, by use of optical properties that respond to products formed between the indicator and all aldehydes.

Figure 5A:
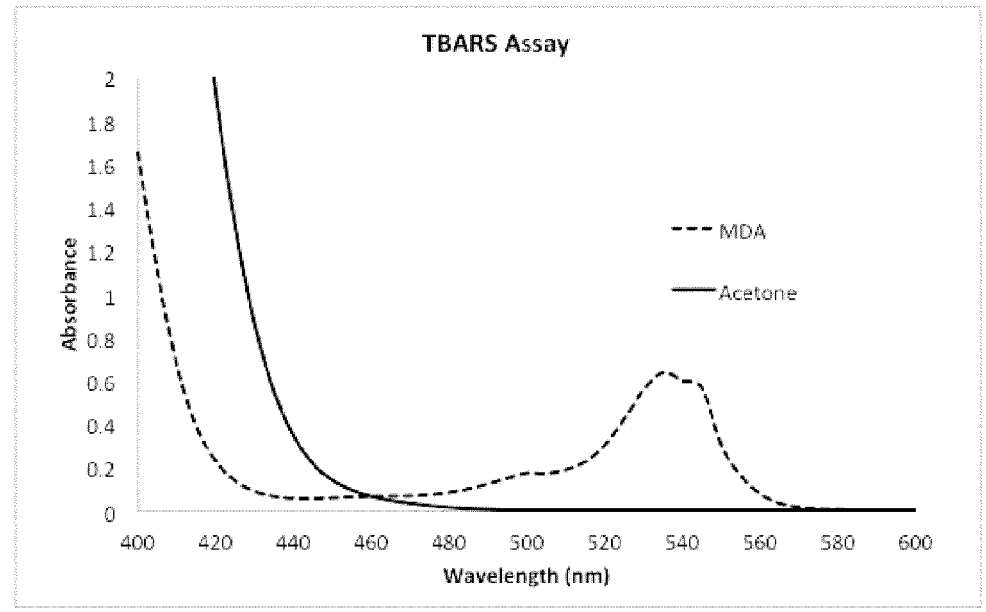
In FIG. 5a, one curve represented by the dashed lines represents the absorbance spectrum due to the product of the reaction between 2-thiobarbituric acid and a sample containing 25 µM malonaldehyde using the conditions stated in this invention, performed in liquid phase. The solid line represents the absorbance spectrum obtained when a sample of ~13.6 M (approximately 6 orders of magnitude more than that of the MDA tested) was reacted under otherwise identical conditions.
Figure 5B:
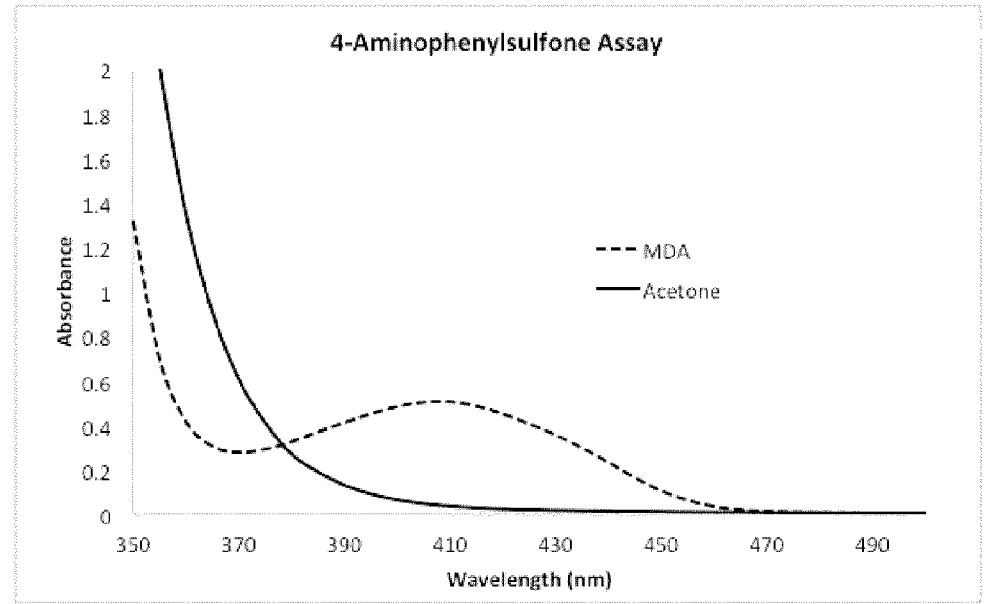
In FIG. 5b, one curve represented by the dashed lines represents the absorbance spectrum due to the product of the reaction between the aromatic amine indicator 4-aminophenylsulfone and a sample containing 25 µM malonaldehyde using the conditions stated in this invention, performed in liquid phase. The solid line represents the absorbance spectrum obtained when a sample of ~13.6 M (approximately 6 orders of magnitude more than that of the MDA tested) was reacted under otherwise identical conditions.

FIG. 5 illustrates the use of specific optical properties to selectively detect or quantify malonaldehyde-indicator products vs. a non-aldehyde compound containing a carbonyl group (acetone in this example). In FIG. 5a, one curve represents the absorbance spectrum due to the product of the reaction between 2-thiobarbituric acid and a sample containing 25 µM malonaldehyde using the conditions stated in this invention, performed in liquid phase. Under identical conditions, a sample containing 25 µM acetone did not yield any detectable change in the optical properties of the solution. In fact, when a sample of neat (100%=13.6 M, or approximately 6 orders of magnitude more than that of the MDA tested) acetone was allowed to react, the spectrum that was obtained revealed strong absorbance below 450 nm, but no absorbance in the ~525 nm region is which the MDA-TBA product is measureable. Similar results were obtained using an aromatic amine indicator, as depicted in FIG. 5b. Again, a sample containing 25 μM malonaldehyde was allowed to react using the conditions stated in this invention, performed in liquid phase. Under identical conditions, a sample containing 25 μM acetone did not yield any detectable change in the optical properties of the solution at wavelengths above 400 nm at which the MDA product with the aromatic amine indicator, 4-aminophenylsulfone in this example) is measurable.

Figure 6A:
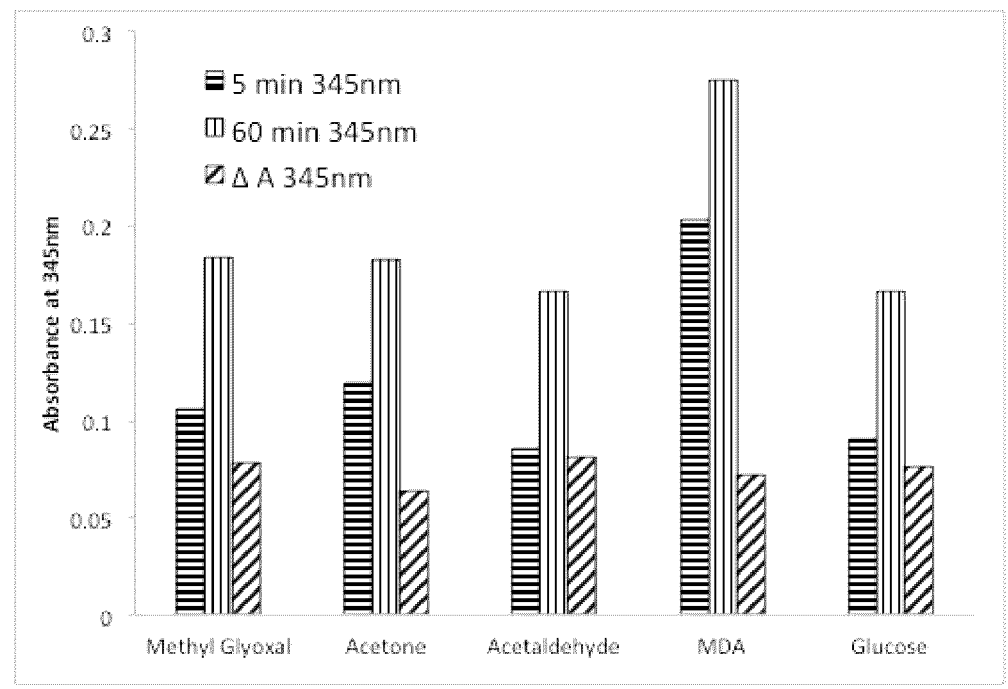
FIG. 6a compares the absorbance of light at 345 nm after reaction for 5 or 60 min of equimolar quantities of various carbonyl-containing compounds with 4-aminophenylsulfone.
Figure 6B:
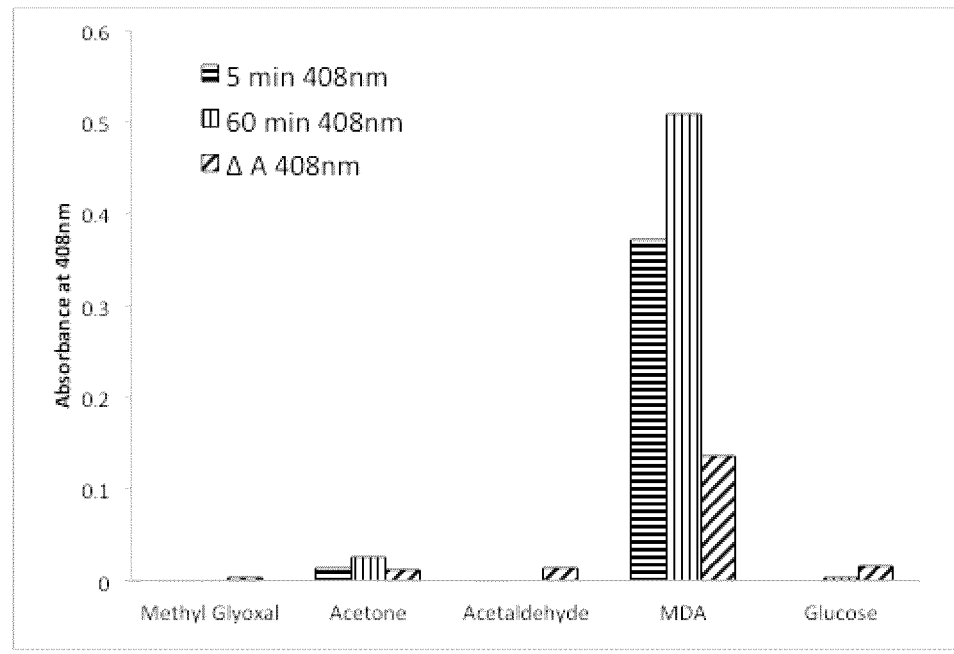
FIG. 6b compares the absorbance of light at 408 nm for the same reactions and same time intervals, and illustrates specificity for MDA at this wavelength.

The utility of invention embodiments for the detection or analysis of a group of carbonyl-containing compounds based on one optical quality (e.g. absorbance or reflectance of light at a specific wavelength) vs. the selective detection or quantification of a specific aldehyde (e.g. malonaldehyde) is further illustrated by FIG. 6. FIG. 6a compares the absorbance of light measured after reaction of equimolar quantities of a group of carbonyl-containing compounds with the aromatic amine indicator, 4-aminophenylsulfone. When the absorbance of light is monitored at a lower wavelength (345 nm in this case) it is observed that all of the test compounds react very quickly with the indicator. In contrast, as shown in FIG. 6b, when the reaction is monitored at a higher wavelength (408 nm in this example with this indicator) only malonaldehyde produces an appreciable change in optical properties. FIG. 6 further demonstrates that the reaction is not instantaneous, and that measurement of the optical properties at multiple time intervals (5 and 60 min in this simple example) permits a kinetic analysis of product formation, thus affording the utility of eliminating interference due to colored substances that are present in the sample without the requirement to separately measure and subtract a blank reading in the absence of indicator.

Figure 7:
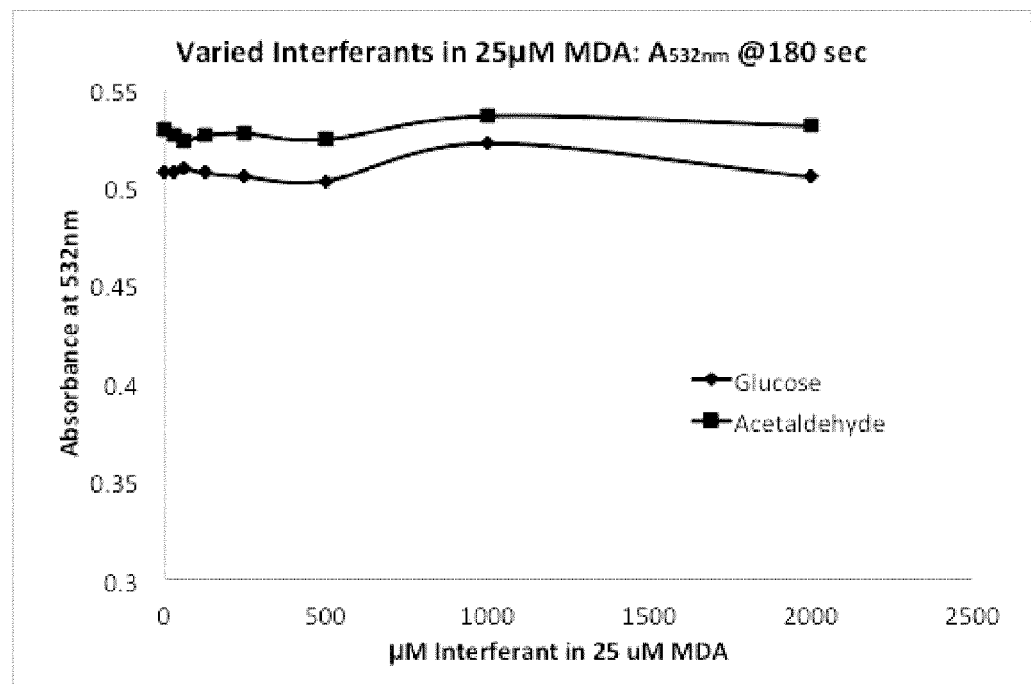
FIG. 7 is a chart illustrating unexpected benefits achieved by one embodiment of the invention using 2-thiobarbituric acid for the determination of MDA that shows the complete absence of interference in the presence of an 80 fold excess of two aldehydes commonly present in biological specimens.

The advantageous relative insensitivity of present embodiments, when used to measure malonaldehyde, to interferences due to the presence of other aldehydes in a sample is illustrated in FIG. 7. Increasing concentrations of two substances that are found in biofluids that are reactive with the 2-thiobarbituric acid indicator using prior methods were added to a sample containing a fixed amount (25 μM) of malonaldehyde. After incubation for 3 minutes, solutions containing up to 80 fold higher amounts of either acetaldehyde or glucose did not have demonstrable effects (positive or negative) on the optical signal for the MDA-indicator complex at 532 nm.

Figure 8:
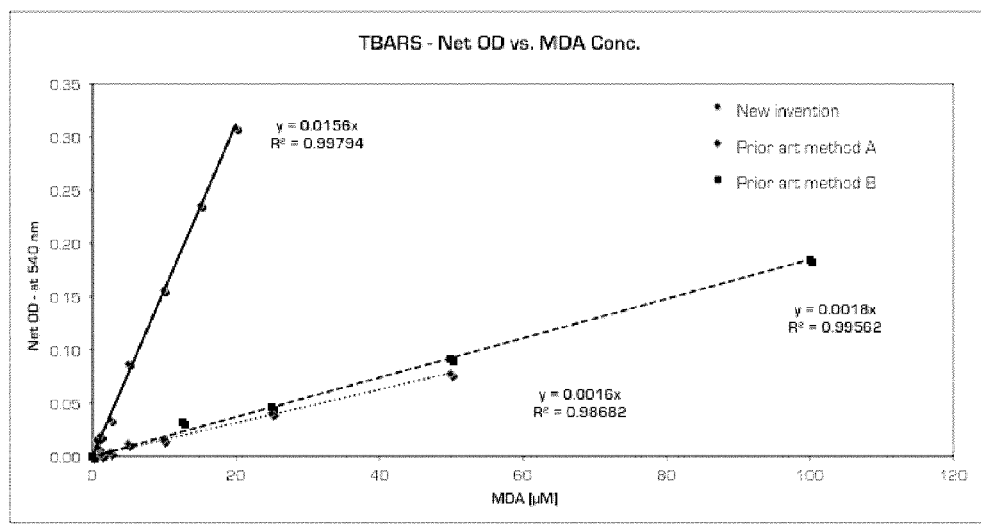
FIG. 8 is a chart illustrating the improved sensitivity of a liquid phase embodiment of the invention involving a 2-thiobarbituric acid indicator to measure MDA where the assay is carried out at room temperature, as compared prior methods (which require applying external heat to the sample—including, for example, boiling for periods of about 1 hour)

The superior sensitivity of embodiments for the measurement of malonaldehyde by monitoring the absorbance of light in a liquid format is illustrated in FIG. 8, which depicts standard curves obtained for absorbance at 540 nm versus increasing concentrations of malonaldehyde for the method described herein vs. two commercial kits for malonaldehyde detection that employ prior art.

Figure 9:
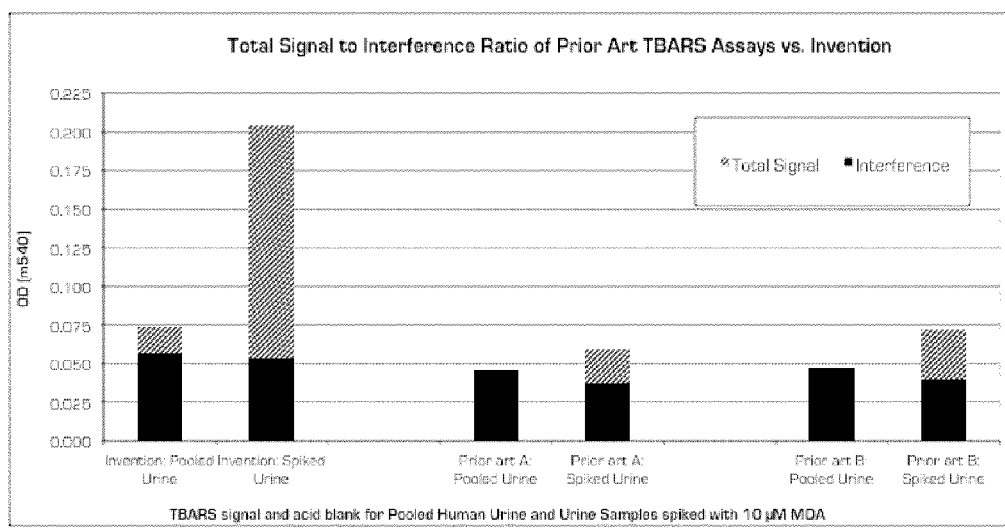
FIG. 9 is a chart illustrating the improved signal to noise ratio for a room temperature liquid phase embodiment of the invention involving a 2-thiobarbituric acid indicator to measure MDA as compared to prior methods for liquid phase analysis of MDA which require applying external heat (for example, boiling the reaction mixture for periods of around 1 hour).

The reduced levels of interfering substances, either endogenous or produced as the result of the reaction of acid with endogenous substances in a biological sample, that are detected using invention embodiments compared to prior art are depicted in FIG. 9. In this study, a pooled human urine sample with and without 10 μM of malonaldehyde, were analyzed using a liquid phase embodiment of the present invention. For each method, a blank was also analyzed in which all components were present except the 2-thiobarbituric acid indicator. For all three methods, an appreciable absorbance at 540 nm is observed after the reaction is allowed to go to completion (end point method). However, given the low sensitivity of prior art methods for malonaldehyde, the entire absorbance at 540 nm is due to this interfering optical signal when prior art methods are employed. In contrast, using the method described in this invention, inclusion of the 2-thiobarbituric acid indicator results in a greater optical change that is due to the formation of the indicator-malonaldehyde product. This is further demonstrated when results are compared for samples with 10 μM malonaldehyde was added. After subtraction of the blank, all three methods yield a signal due to the malonaldehyde-indicator complex, but the signal to noise (background) for embodiments of the invention are much greater, which permits greater accuracy.

The results presented in FIG. 9 are for a reaction that is allowed to proceed to completion, and the background signal observed may be due to endogenous colored substances in the urine sample and/or substances generated by reaction of endogenous substances with acid. The lower temperature and weaker acid employed in this embodiment suggests that most if not all of the background color is due to endogenous chromogens in the sample. Therefore, by performing the reaction kinetically (measuring the change in color with time) one can analyze specifically for malonaldehyde without the necessity of measuring and subtracting a blank. This embodiment is particularly useful for analyses performed by relatively unskilled individuals when applied with a device that monitors the change in optical quality of the sample with time.

Figure 10A:
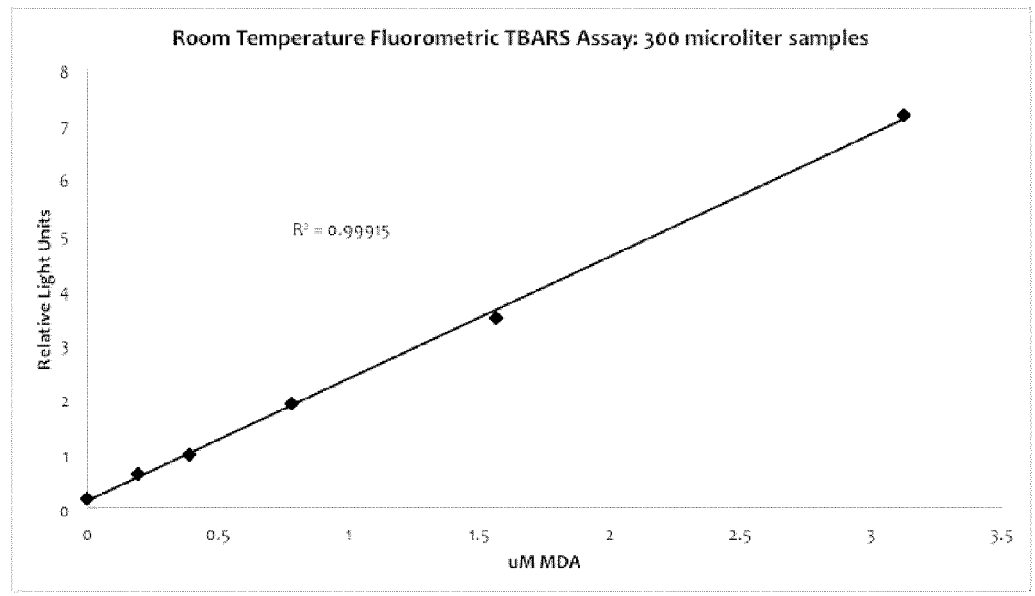
FIG. 10 illustrates the unanticipated high sensitivity of one liquid phase embodiment of the invention involving fluorometric detection of the 2-TBA-MDA product for the detection of malonaldehyde. Similarly.
FIG. 10b illustrates that a second liquid phase embodiment of the invention that employs 2-TBA as the indicator and also includes DMSO can detect MDA at nanomolar levels, well below detection limits reported for prior art fluorescent methods.
Figure 10B:
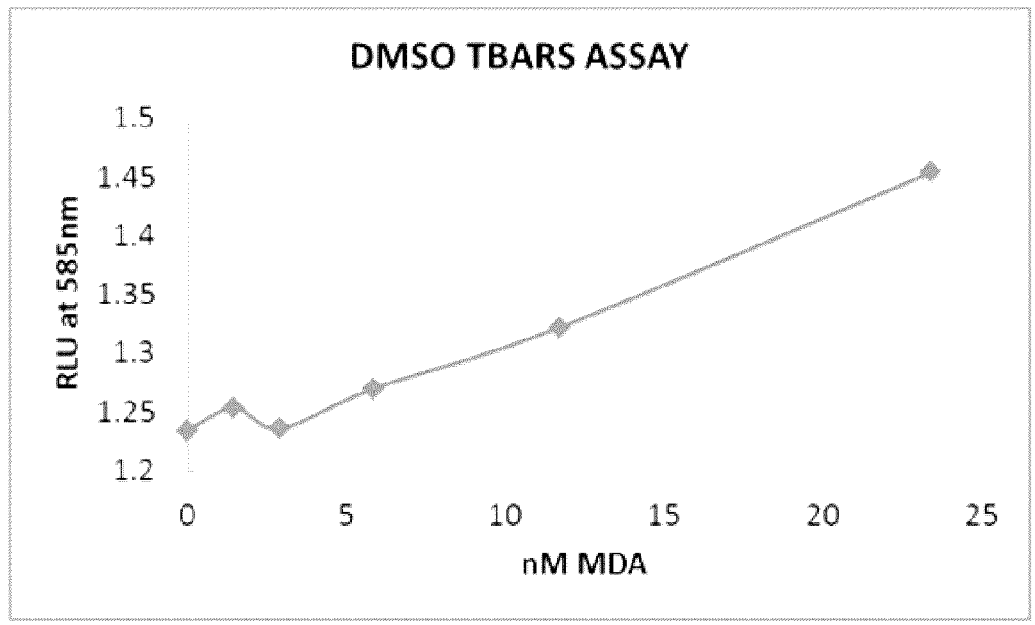

Even greater sensitivity for malonaldehyde, with even less interference, is possible for embodiments involving an indicator that forms a fluorescent product upon reaction with malonaldehyde. This is illustrated in FIG. 10a-10b which illustrates that very sensitive specific fluorescence quantification of MDA can be achieved over a broad range under these conditions, ranging from over 3 micromolar to as low as 5 nanomolar (in this case by illuminating the sample at ~532 nm and monitoring the fluorescence of the MDA:2(TBA) product at ~585 nm).

Solid Medium Embodiments

Again, invention embodiments may be carried out in either liquid format or solid form (with an example being liquid droplets or microdroplets held within the interstitial spaces, or on the surfaces of, a solid substrate). In many commercially valuable applications, a solid format provides unique advantages and benefits. As an example, in some invention embodiments a so-called dip-stick, swab or pad format can be adopted for sample testing. This format is particularly useful for applications such as bodily fluid (urine, saliva, other) testing, agricultural/food testing, and the like. In such applications portability and ease of use are particularly advantageous. A sample (biological or agricultural) can be made to contact an apparatus of the invention (a dip-stick, swab or other solid medium), with a resulting change in the optical characteristics of the apparatus indicating the presence and/or the concentration of a specific aldehyde or of compounds possessing an aldehyde functional group.

Advantageously, through invention embodiments the solid phase test media (dip-stick, swab, pad, other) can be prepared in bulk, stored and then transported to field testing locations (such as a clinic, home, school, place of employment, drugstore, etc.), and field testing then performed by low-skilled operators or even users. After exposure to a bodily fluid, agricultural material or other test sample, the solid phase media can be optically measured in the field (using a portable instrument, for example), or in some embodiments may be transported to a measuring location.

In such invention embodiments, an apparatus of the invention includes a solid medium containing, retaining, or otherwise holding the nucleophilic compound, acid and any other reagents (with an example being stannous chloride) of the inventive embodiment. Upon contact with the liquid phase aldehyde-containing sample, rapid diffusion of the sample, dissolution of the solid phase reagents, and a reaction as described above occurs. A variety of solid mediums are suitable for use in different invention embodiments, but in many they are selected for (a) their ability to hold the reagents before and after reaction, (b) for allowing good interface with a liquid sample containing the aldehyde, (c) for low reactivity with the immobilized acid to prolong the shelf life of the device, (d) for enhance reflective or other optical properties, (e) for well characterized and control surface chemical and physical characteristics including surface tension, and surface acidity and/or (f) for the presence of additives that enhance the sensitivity and/or specificity of the reaction of the indicator with the aldehyde being measured. Most important, the solid medium should be selected and optimized for indicating a color change or other optical property change through the reaction of the nucleophilic compound held thereon.

With regard to providing low reactivity during storage, an important benefit of many embodiments includes their ability to be transported and/or stored for prolonged periods without degradation through reaction. In some embodiments, an apparatus of the invention with reactants held thereon is stored for a period of at least one month, in other embodiments at least 2 months, in others at least 3 months, in others at least 6 months, and in others longer periods. In each of these cases, minimal or no degradation of the apparatus occurs during storage through catalyzing changes to the indicator or solid matrix.

An example suitable solid medium is a fiber matrix featuring entangled fibers. The entangled fiber structure is useful to provide a relatively large surface area for reaction interface; good interstitial surface spaces and optimal porosity to promote rapid diffusion and dissolution of the solid reagents held therein; a good structure for retaining the nucleophilic compound, acid and any other materials present; and is useful for allowing measurement of color change through reaction. In many embodiments it should be suitable for withstanding heating in a dryer, which may be performed to dry the liquid solution containing reaction reagents of the invention.

Such matrices are known. They may be non-woven hydro, thermal, electro or other entangled matrices of glass, silica or polymer fibers, including polyester or polystyrene fibers. Fibers of various diameters and lengths may be selected, and density of entanglement may also be varied to suit particular applications. Cellulose fibers may be used in some applications, although the selection of acid may limit the usefulness of cellulose, especially for prolonged shelf life, due to the typical acid-catalyzed hydrolysis of celluloses. Examples of suitable matrices are available from Ahlstrom, Mount Holly Springs, Pa. and other suppliers, with one particular example under the tradename Ahlstrom 8975 (which is made using glass microfibers having a 50 g/m$^2$ basis weight and are of 0.28 caliper).

The fiber matrix may be formed in any desired shape for a particular application. In some example embodiments, it is shaped as a relatively thin pad, swab or dipstick suitable for contact and interaction with a desired liquid sample. For example, a dipstick form may be useful for immersion in a liquid sample (with one example being urine), and a swab for swiping saliva from a tongue, blood/other liquid extract from meat surface/drippings, or the like.

Typically, solid phase "dip-stick" technologies measure the reflectance of light from the surface of the solid matrix in which the reaction takes place. Using either of the classes of nucleophilic indicator compounds described (see FIGS. 1 and 2 for examples), this embodiment may be performed by the measurement of reflectance in solid phase embodiments at appropriate wavelengths. In order to eliminate potential interference due to endogenous chromogens present in complex biological samples, the kinetics of product formation may be monitored using either active methylene or aromatic amine indicators. Further, as in the case of the most sensitive liquid phase embodiment of this invention, for indicators that form a fluorescent product with malonaldehyde, the detection and/or measurement of this specific aldehyde can be performed with greater sensitivity and specificity.

Figure 11:
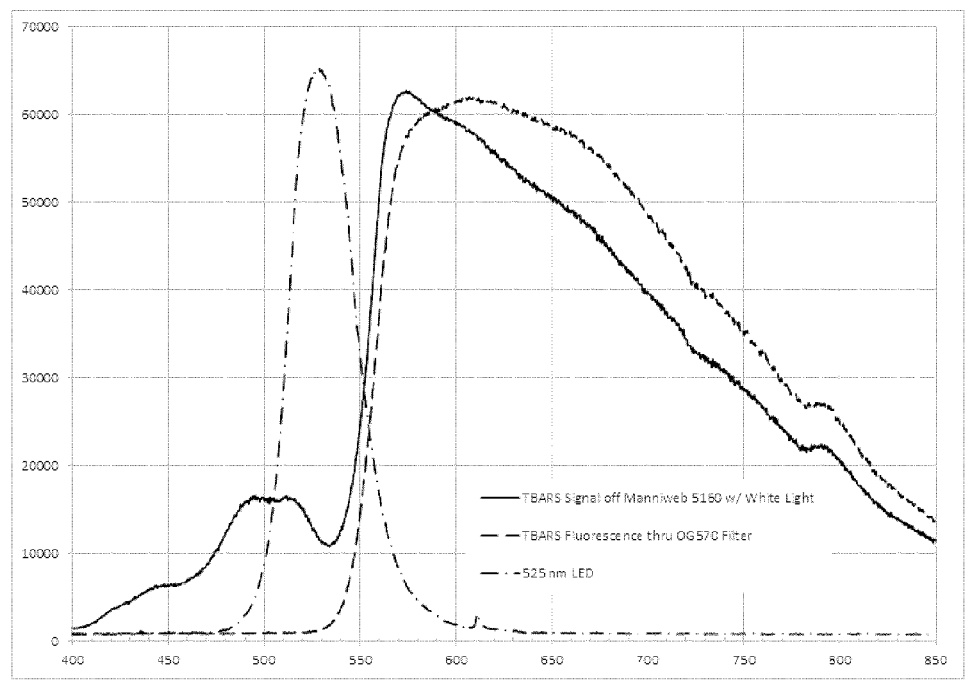
FIG. 11 is a chart that superimposes three spectra on the same graph for one of the solid phase embodiments of the invention. Two spectra illustrate optical changes that occurred during the reaction when 2-thiobarbituric acid—MDA product is formed. The first spectrum shows the relative reflectance of an incandescent filament white light source off of the solid phase, that has on its surface the 2-thiobarbituric acid embodiment of the invention (solid line). This spectrum clearly illustrates both an absorbance of light at 535 nm as well as the production of a fluorescent signal that peaks at 575 nm. The second spectrum (dashed line) illustrates light that is measured when the solid phase surface is illuminated with a 525 nm light emitting diode (LED) and the reflected signal is restricted by a high-bandpass filter (Schott Glass OG-570) to monitor only the fluorescence emission spectrum of the TBA:MDA complex. The third spectrum (dotted and dashed) shows the irradiance spectrum of a 525 nm LED.

FIG. 11 illustrates optical properties that are very suitable for the measurement of malonaldehyde in a solid matrix embodiment using an optical device that illuminates the sample at one wavelength using a light emitting diode that excites the MDA-2-TBA product at ~525 nm, combined with a long bandpass filter (in this case one that blocks essentially all light below 570 nm) placed between the sample and the detector. Overlaid on this graph are the emission spectrum of the 2-TBA-MDA product that is obtained upon illumination at 525 nm, and the spectrum of a light that passes through a nominal ~570 nm bandpass filter. Typically, analysis of TBA:MDA products using LED light sources employ a 525 nm LED to excite the product and, in fluorescence assays a bandpass filter may be employed to specifically measure the fluorescence of the 2-TBA-MDA product formed in some embodiments of this invention. Note the close correlation between the spectrum of light that is emitted when white light is shown on a solid matrix TBA-MDA product and how closely it compares to the fluorescence emission of the TBARS chromogen excited at 525 nm.

The choice of solid matrix for the detection or measurement of aldehydes can be particularly important in different invention embodiments. Even when a relatively weak acid is immobilized in a solid matrix, the matrix should be relatively resistant to chemical decomposition due to prolonged contact with the acid to prolong shelf life. Thus, cellulosic polymers that are widely employed in solid phase "dip stick" devices are not suitable for some invention embodiments since they have a relatively short shelf life. Matrices comprised of woven glass fibers are more stable, but many such matrices have low tensile strength and are not well suited to large scale manufacture, which can employ, for example, using rollers to dip the matrix into an impregnating solution and then drying the matrix by pulling it through a dryer with heated air. It has been discovered that some woven glass matrices that contain relatively acid-resistant binders have sufficient tensile strength and acid resistance to allow for ease of manufacturing for immobilization of the acid and indicator and relatively long shelf life. Again, an example of one such a matrix is available under the tradename Ahlstrom 8975.

An unanticipated advantage of some invention embodiments that can significantly benefit the sensitivity of solid phase methods for the analysis of malonaldehyde are the inclusion of solid matrices comprised of polyesters. The manufacturing process for the production of some polyesters includes the addition of fluorescent whiteners during the production process. Such examples include those available under the trade names Manniweb 5160 and Lydell 9816 available from Lydall Manning Corporation of Try, N.Y. Although it might be expected that such fluorescent whiteners would interfere with the fluorescent detection of a fluorescent product formed between an aldehyde and an indicator, it has been discovered that polyesters containing whiteners provide an unanticipated significantly enhanced fluorescence signal due to the malonaldehyde: 2-thiobarbituric acid product.

Figure 12:
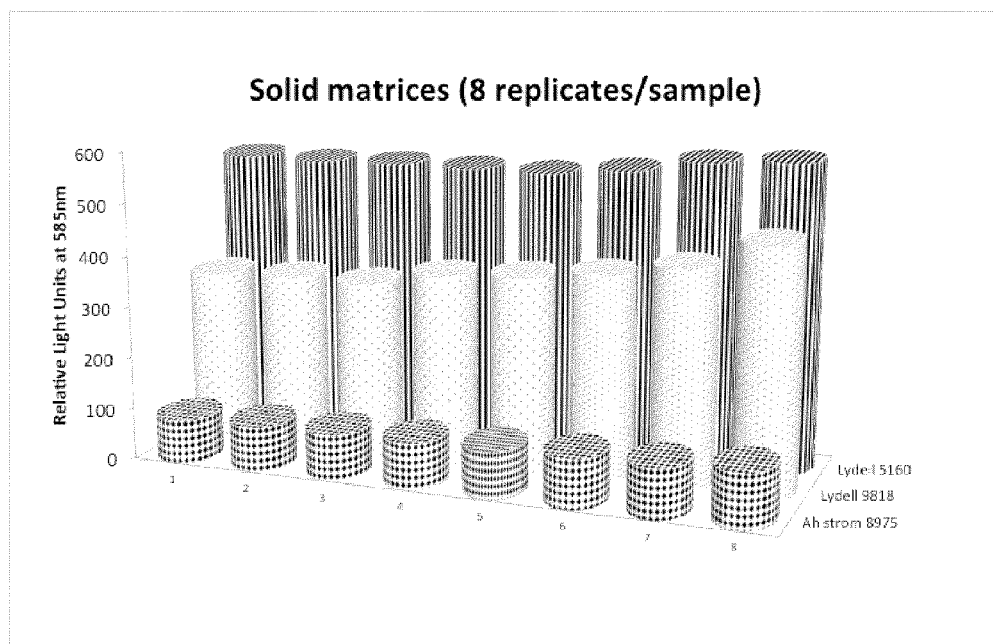
FIG. 12 illustrates the relative performance of various different commercially available solid matrices in the solid phase invention embodiments.
Figure 13:
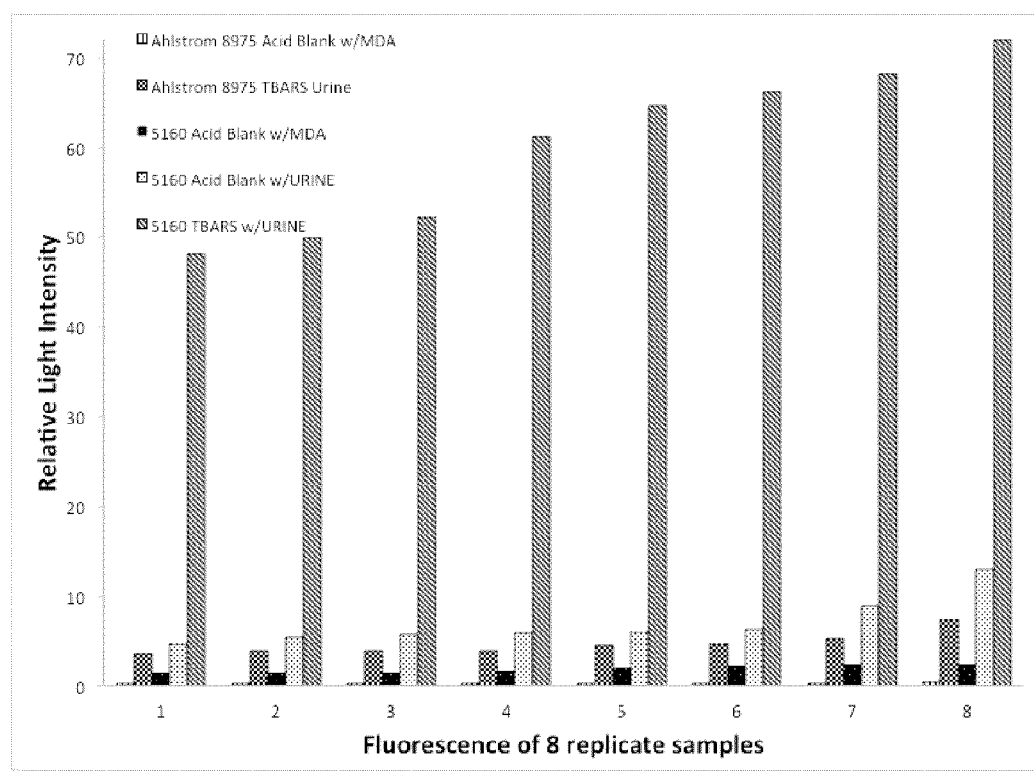
FIG. 13 illustrates the fluorescence signal obtained for human urine samples in solid phase embodiments of the invention employing various glass and polyester solid matrices, and the unanticipated significantly greater signal obtained compared to the acid blank for a polyester matrix containing fluorescent whitening agents.

This is illustrated in FIG. 12 in which eight replicates of one concentration of malonaldehyde were reacted in a solid phase embodiment that was immobilized in three matrices, one comprised of woven glass and the others comprised of polyesters containing whiteners. FIG. 13 illustrates that the observed strong fluorescence signal obtained for polyester matrices is not due to the endogenous fluorescence of the matrix and does not increase any background fluorescence due to other components in a biological fluid such as human urine. The fluorescent whitener may be imbibed or otherwise incorporated onto or into the solid medium or matrice. The technical reasons behind these surprising results are not presently fully understood, but may involve a broader and stronger fluorescent signal due to interactions between the fluorescent whitener(s) and the fluorescent 2-TBA-MDA product.

In some invention embodiments, a liquid test solution is prepared and introduced onto a solid medium of the invention through spraying, dripping, rolling, painting, immersion or other method. The solid medium is then dried leaving solid phase reagents held thereon. In some embodiments, micro drops of liquid phase reagents or reagents contained in hydrogels, or emulsion particles may also or alternatively be held through capillary or other action on the solid medium. Loading of the solid matrix may be as desired and suitable for particular applications and reagents.

When the solid medium of the invention comes into contact with a liquid sample containing an aldehyde, the solid phase reagents held on the solid medium react—either while remaining in solid phase or after partially or completely dissolving into solution. Alternatively, liquid phase reagents held on the solid medium react. Some portion of the reaction products are retained on the solid medium following reaction. This results in changes to the optical properties of the solid medium as compared to pre-reaction. A color or fluorescence change occurs and can be measured, with the resulting measurement indicating the presence of and/or concentration of an aldehyde. It is noted that for convenience an optical property change of the solid medium may be referred to herein for convenience, although it will be appreciated that such change may actually only occur to chemical compounds held on the solid medium but not the underlying medium itself.

Measurement of Optical Changes

In various invention embodiments, optical changes are measured between a ore-reaction indicator (the nucleophilic compound) and a post reaction chromophore. The optical changes indicate that reaction with an aldehyde occurred, and can thereby be used to confirm the presence and/or estimate the concentration of the aldehyde. Those knowledgeable in the art will appreciate the various suitable steps for making such measurements, with the result that for sake of brevity detailed discussion is not necessary herein. Brief discussion, however, will be helpful.

Use of a spectrometer may be made to illuminate a sample with light across a desired wavelength. Absorbance of such wavelength light indicates the presence of a particular chemical structure. In various invention embodiments that utilize 2-TBA as a nucleophilic compound, absorbance of light around the 532 nm wavelength indicates the presence of the reaction product with an aldehyde.

In solid phase embodiments, as illustrated in Figures referenced above, the measurement device may be comprised of a reflectometer to illuminate a sample with light across a desired wavelength. The reflectance of such wavelength of light indicates the presence of a particular chemical structure. In various invention embodiments that utilize 2-TBA as a nucleophilic compound, the decrease in reflectance of light around the 532 nm wavelength indicates the presence of the reaction product with malonaldehyde, and at approximately 440 nm for monoaldehydes that are not conjugated. Other wavelengths may be used as desired that are known optimal for other indicators. In some embodiments care can be taken to avoid using a solid medium that causes background interference with any particular wavelength of illumination.

In other solid phase embodiments, as illustrated above, the measurement device may be comprised of a fluorometer to illuminate a sample with light across a desired wavelength range. The fluorescent signal produced upon the interaction of the incident light with the analyte molecule (e.g. a 2:1 product formed between 2-thiobarbituric acid and malonaldehyde) indicates the presence of the reaction product with an aldehyde.

In addition to determining the presence of a particular material, the concentration of it may also be determined through invention embodiments. Method and apparatus embodiments include several steps for doing so. One is measuring absorbance of the chromogen in solution with the light beam passing through the solution, being measured by a detector on the exiting side of the sample. Another is by reflectance with the light beam being measured incident from the solid surface, going through the liquid phase which is situated on the surface or within the interstitial spaces of the solid substrate. Still another is to measure optical changes over time to estimate a reaction rate and correlate this to concentration. And still another is to measure more than one wavelength of light: (a) at a primary wavelength where the signal measured is proportional to both the product formed, as well as that of a known interference, (b) at known isosbestic points (wavelengths where extinction coefficients for both the initial reactants and final product are the same) where the signal that is measured is only proportional to the interfering substance, and or (c) an additional wavelength where the signal is proportional to a degradation product formed as the reagent on the substrate ages with time. These multiwavelength measurements can then be used to both analyze and determine the concentration of the aldehyde, but also correct for interferences, sample volume variations, and assure the quality of the result in spite of aging.

Invention embodiments achieve important benefits over the prior art in terms of aldehyde detection sensitivity and accuracy. An embodiment of the present invention was able to detect the presence of malondialdehyde in a sample to nanomolar sensitivity, while a method of the prior art run under identical conditions was limited to detecting the malondialdehyde only after concentration had reached the micromolar level. Thus the inventive embodiment achieved a detection threshold sensitivity of an order of magnitude over the prior art.

It will be appreciated that various invention embodiments discussed herein achieve many other important advantages and benefits over the prior art. These include, but are not limited to characteristics that lead to a significantly improved ability to be used in the field without the requirement for highly trained operators. Put simply, invention embodiments lend themselves to being taken out of the laboratory and used at low cost in the field. As a particular example, apparatuses of the invention including solid matrix test mediums may be made in bulk, stored without contaminating reaction, shipped to field locations, and then tests performed in the field with the solid matrix without requiring highly skilled operators. In some applications, test subjects themselves may use the solid matrix to test their own bodily fluids.

As an example, invention embodiments achieve reduced reaction times and temperatures as compared to those of the prior art. Embodiments of the invention can be initiated at room temperature, and go to completion in times of no more than about 10 minutes, no more than about 20 minutes, no more than about 30 minutes, or other periods depending on reagents and other factors. Reaction temperatures can be maintained at room temperature, or in some embodiments may reach somewhat elevated temperatures that are no more than about 25° C., 30° C., 35° C., 40° C., 50° C. or others depending on reagents and other factors. This represents a significant advantage over prior art methods that required significantly elevated temperatures and reaction times of greater than 60 minutes, 90 minutes or more.

The elevated temperatures and input heat required by most prior art methods not only leads to increased energy and slowed processing, but further can significantly complicate testing procedure and results. Heating strong acids to significantly elevated temperatures can present significant safety hazards that necessitate specialized laboratory settings and highly trained operators. Additionally, heating to significant temperatures over prolonged periods can create undesirable effects in the test sample that interfere with accurate measurement of aldehydes. Unwanted byproducts can be produced that create background interferences or otherwise mask the actual aldehyde concentration.

Indeed, at least some methods of the prior art when applied to applications such as urine testing required "subtraction" of a blank sample to correct for interfering compounds. As an example, in a prior art 2-thiobarbituric acid urine assay test, the necessary heating of the urine sample for 30 minutes at 95° C. does generate a signal at 532 nm that interferes with the TBARS assay result. This necessitates the subtraction of a sample blank. An advantage of invention embodiments is that no heating is required, with the result that interfering compounds are not produced (or are present in a much lower concentration). No subtraction of a "blank" sample is required.

To illustrate and quantify this benefit, the results of an experiment using freshly collected urine, shown in FIG. 9, was performed using the catalytic 2-thiobarbaturic acid in 10% tosic acid in DMSO (labeled invention). The 2-TBA/tosic acid solution was added to a urine sample (3:1) and allowed to incubate at room temperature for 30 minutes. In parallel, equal amounts of the same urine sample were analyzed using two commercial products that employ 2-TBA and different acids (labeled prior art A and Prior Art B). Following the instructions provided, the prior art methods were subjected to heat in a boiling water bath for 60 minutes. In each case a second set of urine samples were treated identically, but the 2-TBA was omitted from the reaction mixture. The reaction mixtures that did not contain 2-thiobarbituric acid, still gave some signal at 540 nm, as this is where the 2-thiobarbaturic acid assay is measured. In the absence of 2-TBA, the room temperature method of this invention showed an absorbance of 0.057 A, while the prior art methods had an absorbance of 0.046 and 0.047 A, which illustrates the significant potential contribution of interfering substances to the analysis of MDA using the 2-TBA method (with or without heat).

Further comparison of the signal due to the absorbance of light by the MDA-TBA complex, versus the absorbance due to other substances in urine samples after incubation in the absence of the 2-thiobarbituric acid indicator (i.e. noise or background) using the method of this invention vs. two standard embodiments of prior art, both of which involve heating the sample in acid is depicted in FIG. 9, which shows the significant improvement in the signal to noise values obtained by the method of this invention vs. prior art methods.

Figure 14:
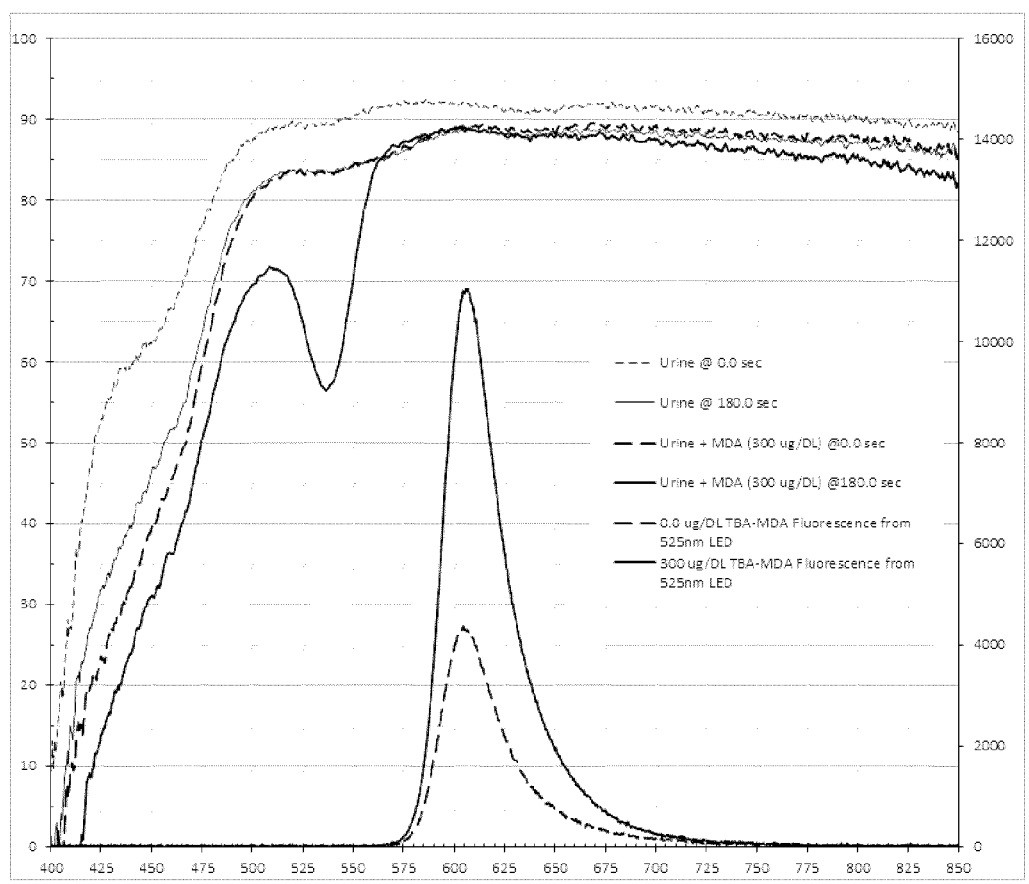
FIG. 14 illustrates white light reflectance and fluorescent irradiance spectra during an application of a fluorescence solid phase embodiment of the present invention for the specific analysis of MDA in human urine, and in the same urine sample to which MDA 300 µg/dL of synthetic MDA was added.

Another illustration of the application of the present invention to the specific analysis of MDA in biological samples is provided in FIG. 14, in which the spectra are provided for a human urine sample applied to a solid matrix composed of polyester and containing whiteners (Manniweb 5160). There is a clear and broad difference between the spectra obtained immediately after adding the urine to the 2-TBA/tosic acid solid matrix device, and that which is obtained after the reaction has progressed for 180 sec. at room temperature. Addition of a second TBA molecule to the complex creates the characteristic peak of the 2:1 product between 2-TBA and MDA at approximately 535 nm. This peak, even at low malonaldehyde concentrations found in biofluids, is quite fluorescent as illustrated. To further illustrate the changes that occur during the reaction of 2-TBA with MDA 300 μg/dL of synthetic MDA was added to the same urine sample and the spectra were measured at 0 and 300 seconds. At this concentration of MDA (approximately 1000× that which is typical for a urine sample, the complex that is formed is believed to "stack up" and thus quench the fluorescence signal. The complex at this point becomes deeply RED and the solid reflectance line moves dramatically to the right. These data support the fluorescence of the 2-TBA:MDA complex because, unlike in absorbance, where there is a disappearance of signal during this reaction, the appearance of a strong light signal is observed.

Figure 15:
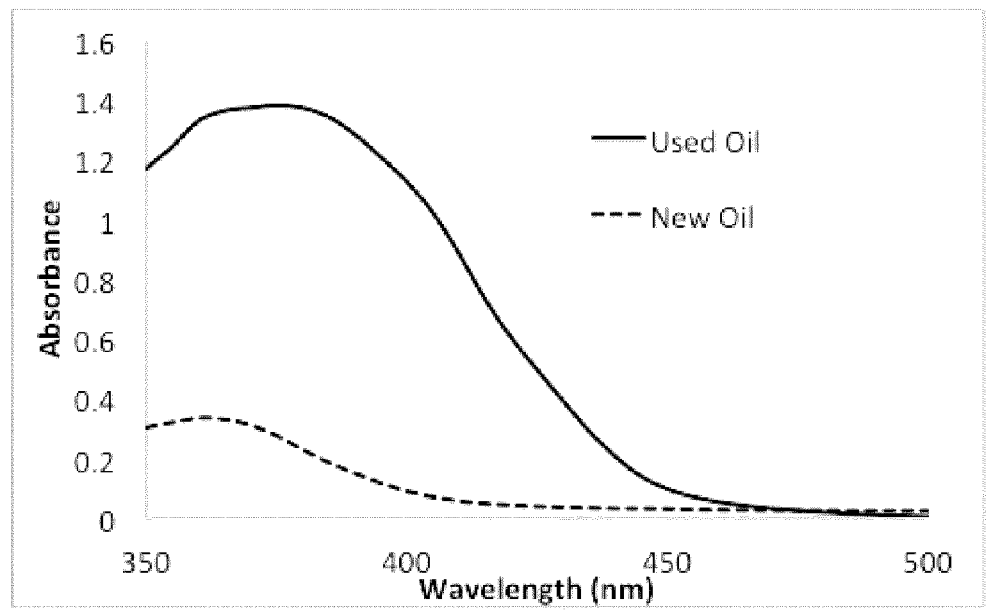
FIG. 15 illustrates use of an aromatic amine indicator for room temperature measurement of aldehydes in fresh vs. used cooking oil.

To illustrate another application of the present invention, an experiment was conducted in which the absorbance spectrum of new vs. used cooking oil was determined after reacting the two samples with an aromatic amine indicator at room temperature in a low concentration of hexamic acid. Results are illustrated in FIG. 15. The aldehydes and other carbonyl-containing compounds derived from the cooking process gives rise to a very large increase in the absorbance of light, centered at approximately 375 nm, by the complexes formed by these compounds with the aromatic amine indicator.

Various embodiments of the invention have been illustrated herein above and in the attached Figures. Such discussion and illustration is not intended to limit the scope of the invention as claimed, but instead by way of presenting some illustrations of various embodiments. Those knowledgeable in the art will appreciate numerous modifications and replacements using equivalents can be made.

What is claimed is:

1. A method for detecting the presence of an, aldehyde in a sample comprising the steps of:
    exposing the sample at or near room temperature to a test medium to catalyze the formation of optically detectable quantities of a product within a time period of no more than 60 minutes and without applying any external heat to the sample or test medium, the test medium comprising an indicator that is a nucleophilic compound having acidic protons at the nucleophilic center and at least one acid;
    wherein the aldehyde is malonaldehyde and wherein the product is a trimeric product formed from the reaction of one mole of malonaldehyde molecule with two moles of indicator; and
    measuring optical changes that occur as a result of the catalysis.

2. A method as defined by claim 1 in which the indicator is an active methylene compound.

3. A method as defined by claim 2 in which the indicator is one of a barbituric acid and its derivatives.

4. A method as defined by claim 2 in which the indicator is 1-methyl-2-phenylindole.

5. A method as defined by claim 1 in which the indicator is one of an aromatic amine and a Schiff reagent.

6. A method as defined by claim 1 in which the indicator is fuchsin.

7. A method as defined by claim 1 in which the indicator is selected from the group of aniline, 4'-aminoacetophenone, ethyl p-aminobenzoate, 4,4'-sulfonyldianiline and p-nitroaniline.

8. A method as defined by claim 1 in which the indicator is selected from the group of 4-hexlylresourcinol, N-methylpyrrole, azulene and indole.

9. A method as defined by claim 1 wherein the at least one acid comprises a sulfonic acid.

10. A method as defined by claim 1 wherein the at least one acid comprises one or more of para-toluene sulfonic acid, benzene sulfonic acid, and hexamic acid.

11. A method as defined by claim 1 in which the indicator and the at least one acid are held on a solid matrix and stored for a period of at least 1 month without catalyzing changes to the indicator or the solid matrix prior to exposure to the sample.

12. A method for detecting the presence of an aldehyde as defined by claim 1, wherein the test medium is a solid, and the method further comprises the steps:
preparing the solid test medium by placing the indicator and the at least one acid on the solid test medium;
subsequently storing the solid test medium for a first time period of at least 1 month without catalyzing changes to the indicator or the test medium;
subsequently transporting the solid test medium to a field test site;
collecting the test sample at the field site;
wherein the step of exposing the sample at room temperature to the solid test medium is performed at the field test site; and,
wherein the step of measuring the optical changes comprises measuring optical changes to the solid test medium and is performed at the field site within a second time period of no more than 60 minutes from the step of exposing the test sample to the solid test medium.

13. A method as defined by claim 1 wherein the step of measuring the optical changes that occur further comprises measuring an aldehyde concentration.

14. A method as defined by claim 1 wherein the step of measuring the optical changes that occur further comprises measuring an aldehyde concentration through steps of taking multiple measurements of the optical changes over time to determine a rate of reaction.

15. A method for detecting the presence of an aldehyde in a sample comprising the steps of:
exposing the sample at or near room temperature to a test medium to catalyze the formation of optically detectable quantities of a product within a time period of no more than 60 minutes and without applying any external heat to the sample or test medium, the test medium comprising an indicator that is a nucleophilic compound having acidic protons at the nucleophilic center and at least one acid; wherein the indicator and acid are solid phase, the method further comprises the step of dissolving the indicator and acid into liquid phase, and the liquid phase further comprises dimethylsulfoxide; and
measuring optical changes that occur as a result of the catalysis.

16. A method for detecting the presence of an aldehyde in a sample comprising the steps of:
exposing the sample at or near room temperature to a test medium to catalyze the formation of optically detectable quantities of a product within a time period of no more than 60 minutes and without applying any external heat to the sample or test medium, the test medium comprising an indicator that is a nucleophilic compound having, acidic protons at the nucleophilic center and at least one acid; wherein the sample is a bodily fluid from a human or animal and the aldehyde is malondialdehyde, and wherein the time period is no more than 20 minutes, and wherein the test sample and medium do not exceed 50° C. during the time period; and
measuring optical changes that occur as a result of the catalysis.

17. A method for determining the presence of an aldehyde comprising the steps of:
reacting a nucleophilic compound having, acidic protons at the nucleophilic center and a sulfonic acid with an aldehyde; wherein the aldehyde is monoaldehyde, and wherein the nucleophilic compound and sulfonic acid react with the monoaldehyde and substantially avoid reaction with other dialdehydes, ketones or other interfering compounds in the sample wherein the changes in optical properties correspond to the concentration of the monoaldehyde and do not correspond to presence of other aldehydes, ketones or other interfering compounds; and
measuring resulting optical properties.

18. A method as defined by claim 17 wherein the nucleophilic compound comprises an aromatic amine and the sulfonic acid comprises sulfamic acid.

19. A method as defined by claim 17 wherein the nucleophilic compound comprises an active methylene compound.

20. A method as defined by claim 17 wherein the sulfonic acid and nucleophilic. compound are immobilized onto a solid phase and the acid comprises one or more of an aryl sulfonic acid or a substituted aryl sulfonic acid, and further including the step of providing a stannous chloride reducing agent as a stabilizer.

21. A method as defined by claim 17 wherein the sulfonic acid is solid phase, wherein the nucleophilic compound and sulfonic acid are held on a solid medium, and wherein the step of measuring optical properties comprises measuring a color change that occurs on the solid medium.

22. A method as defined by claim 17 wherein the sulfonic acid comprises one or more of para-toluene sulfonic acid and benzene sulfonic acid.

23. A method as defined by claim 17 wherein the step of reacting further comprises reacting the nucleophilic compound and sulfonic acid in the presence of dimethylsulfoxide, and wherein the step of measuring optical properties comprises measuring a color change.

* * * * *